US008551195B2

(12) United States Patent
Mitchell et al.

(10) Patent No.: US 8,551,195 B2
(45) Date of Patent: Oct. 8, 2013

(54) SEMI-LIQUID CANDLE

(76) Inventors: Robby Craig Mitchell, Ransom Canyon, TX (US); Lesinee Mitchell, Ransom Canyon, TX (US)

( * ) Notice: Subject to any disclaimer, the term of this patent is extended or adjusted under 35 U.S.C. 154(b) by 257 days.

(21) Appl. No.: 12/958,276

(22) Filed: Dec. 1, 2010

(65) Prior Publication Data

US 2011/0127181 A1 Jun. 2, 2011

Related U.S. Application Data

(60) Provisional application No. 61/265,896, filed on Dec. 2, 2009.

(51) Int. Cl.
*C11C 5/00* (2006.01)

(52) U.S. Cl.
USPC .......... 44/275; 431/288

(58) Field of Classification Search
USPC .......... 44/275; 431/288
See application file for complete search history.

(56) References Cited

U.S. PATENT DOCUMENTS

| | | | | |
|---|---|---|---|---|
| 1,905,923 | A * | 4/1933 | MacLaren | 106/230 |
| 4,110,261 | A * | 8/1978 | Newland | 512/4 |
| 4,568,270 | A * | 2/1986 | Marcus et al. | 431/288 |
| 6,855,179 | B2 * | 2/2005 | Roldan | 44/275 |
| 2003/0226311 | A1 * | 12/2003 | Roy | 44/275 |
| 2004/0250464 | A1 * | 12/2004 | Rasmussen et al. | 44/275 |
| 2007/0006521 | A1 * | 1/2007 | Licciardello et al. | 44/275 |

* cited by examiner

*Primary Examiner* — Cephia D Toomer
(74) *Attorney, Agent, or Firm* — Susanne M Moore

(57) ABSTRACT

A composition and method is disclosed for a wickless semi-liquid candle.

15 Claims, 2 Drawing Sheets

22
24
22
20
26

SEMI-LIQUID CANDLE

CROSS REFERENCE TO RELATED APPLICATIONS

This application claims priority to provisional application No. 61/265,896 filed on Dec. 2, 2009 by the present inventor and the application is hereby incorporated by reference in its entirety.

STATEMENT REGARDING FEDERALLY SPONSORED RESEARCH OR DEVELOPMENT

Not Applicable

NAMES OF PARTIES TO JOINT RESEARCH AGREEMENT

Not Applicable

REFERENCE TO SEQUENCE LISTING

Not Applicable

DESCRIPTION OF ATTACHED APPENDIX

Not Applicable

BACKGROUND OF THE INVENTION

1. Field of the Invention

This invention relates generally to scent carrying devices such as candles and more particularly, to wickless candles.

2. Description of Related Art

The marketplace continually seeks a way to satiate society's desire to be surrounded by appealing fragrances whether in their homes, offices, vehicles, or other environments. Scents affect our mood which in turn affects our actions and emotions. The candle industry is a multi-billion dollar-a-year business, ever seeking the next hot fragrancing product. One need only review the large number of granted patents on candle variations to illustrate this demand.

Years ago, the only candles available on the market were traditional solid wicked candles found in a jar or holder. Since then, the marketplace has exploded with variations. U.S. Pat. No. 6,129,771 "Gel Candle and Method of Making, U.S. Pat. No. 6,599,334 "Soy Bean Wax Candles" and "U.S. Pat. No. 6,730,137 "Vegetable Oil Candle" are three examples of such candle variations, each sought to fulfill a specific need.

Possibly the most familiar type of candle to the consumer is the wicked candle in a jar. Wicked solid candles in jars exhibit several disadvantages. The most obvious is smoke, which can discolor adjacent walls, ceilings or personal items. The second is fire, which can be life threatening and extremely destructive. In a traditional wicked jar candle, the wax melts as a result of the heat expelled from the burning wick. A large amount of wax pools in the jar and the jar and the wax both become very hot, causing a potentially messy and dangerous situation if a child or even adult were to touch or overturn the jar. Wicked candles can cause a significant threat to person and property if left unattended or if the consumer forgets to blow out the flame.

In an attempt to eliminate these disadvantages, one of the most important evolutions in the candle industry has been the development of the wickless jar candle, designed to be placed on an electrical warmer in order to release the fragrance. Wickless jar candles eliminate smoke and the risk of fire, as there is no open flame. Unfortunately they do not solve the problem of the glass jar becoming hot or the large amount of hot wax pooling in the jar. Both wicked and wickless solid candles in jars are costly and difficult to ship.

As the marketplace has struggled to solve the dangers associated with smoke, open flame and hot wax, various new products have continued to emerge, including warming fragrance oils, gel candles, liquid candles, and wax blocks. A liquid candle typically consists of a jar containing kerosene or a similar volatile oil, a small amount of fragrance oil and a wick. A benefit of liquid candles and warming fragrance oils is that because there is no solid paraffin one does not need to apply as much heat to release the scent. Less heat means less pooling of hot wax and a jar that is not as hot to the touch. Yet a major disadvantage is that liquid candles do not put forth quite the same scent as traditional solid candles. When a wicked candle burns it releases not only the fragrance trapped within the wax but also the smell of the melting hot wax itself. This gives wicked candles their traditional appealing fragrance and is something that cannot be replicated by warming fragrance oils or liquid candles. Also, pure liquid, as found in liquid candles, is difficult to store, potentially dangerous should a child or pet try to drink it, and can easily spill.

Despite the marketplace explosion of fragrance-emitting products, there is yet a need for a scent carrying device that minimizes mess, danger and shipping cost. There is a need for a candle to throw off a fragrance as similar to a traditional wicked candle as possible, yet be environmentally friendly in its composition, be affordable, be safe and be more versatile than the candle compositions currently available. In addition, the solution should provide a stronger and longer lasting scent than the currently available products and should allow flexibility of use and customization by the customer.

SUMMARY OF THE INVENTION

In accordance with the present invention, a composition and method is disclosed for a novel wickless semi-liquid candle that overcomes the disadvantages described in the foregoing paragraphs.

An objective of the disclosure is a candle composition and method that is less expensive to package and ship and takes up less shelf space.

An objective of the disclosure is a candle composition and method that produces stronger and longer lasting scent than the known wickless candles.

An objective of the disclosure is a candle composition and method that retains the traditional scent associated with melting wax.

An objective of the disclosure is a candle composition and method that is easily storable and usable by the end user.

An objective of the disclosure is a candle composition and method that eliminates smoke and fire hazards.

An objective of the disclosure is a candle composition and method that requires less shelf space but is aesthetic and desirable in appearance.

An objective of the disclosure is a candle composition and method that emits scent at a lower temperature and has a lower melting point than traditional solid candles.

An objective of the disclosure is a candle composition and method that can be packaged in such a way that the user can control the amount dispensed and the resultant scent.

An objective of the disclosure is a semi-liquid candle composition that does not dry out when exposed to air.

An objective of the disclosure is a semi-liquid candle composition that can be easily wiped out of the warmer after cooling.

An objective of the disclosure is a semi-liquid candle composition that provides instant fragrance as opposed to having to wait for a wax block to melt.

Other advantages of the present invention will become apparent from the following descriptions, taken in connection with the accompanying figures, wherein, by way of illustration and example, an embodiment of the present invention is disclosed.

BRIEF DESCRIPTION OF THE DRAWINGS

The figures constitute a part of this specification and include exemplary embodiments to the invention, which may be embodied in various forms. It is to be understood that in some instances various aspects of the invention may be shown exaggerated or enlarged to facilitate an understanding of the invention. To enable more thorough understanding of the features and advantages of the present invention, reference is now made to the detailed description of the invention along with the accompanying figures in which.

DETAILED DESCRIPTION OF THE PREFERRED EMBODIMENTS

Figure 1:
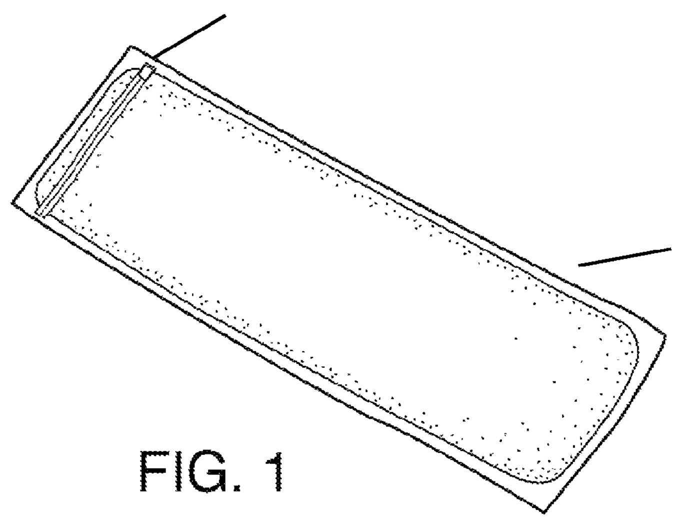
FIG. 1 is a side perspective view of a preferred embodiment of the invention, in packaging.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The ideal fragrance product is one that smells appealing, can expel an intense amount of long-lasting fragrance from a small amount of product, is attractive, safe and relatively inexpensive to package and ship. Ideally such an item would require only a small amount of shelf space at the retailers. The disclosed composition and method poses exactly these and more advantages. The fragrance emitted is similar to the desirable smell of a traditional wicked candle. Because only a small amount of the substance is needed to achieve the same fragrance intensity as a large jar candle, substantially less packaging is used. Shipping costs are reduced. Because the composition and method requires no flame, it is safer and cleaner. Because the melting point and the temperature point at which the scent emits are low, the composition and method is less likely to cause injury.

The disclosed is safer, cleaner, less messy, throws off more fragrance per ounce, is more affordable due to the decreased packaging and shipping costs, and offers the user more variety. It also enables easy storing and use of unused quantities because it maintains a stable semi-liquid consistency at room temperature and up until its melting point. The semi-liquid composition has the benefit of easy clean up as well. Whereas solid wax blocks, once they have been melted and then cooled, require chipping or digging to remove from the dish, the disclosed fragrance product is easily wiped from the dish with a paper towel or rag.

More particularly, the disclosure embodies a wickless semi-liquid candle consisting essentially of at least 40% petroleum jelly by weight, 10-15% resin by weight, 20%-50% fragrance oils by weight and further having a melting point between 90 and approximately 180 degrees Fahrenheit. Colorant or fragrance dye may be added if desired which would comprise a fraction of a percent by weight. The composition achieves uniform consistency, stability and low melting threshold, while capturing unusually high concentrations of fragrance oils. In a second manifestation, the disclosed is a novel squeeze packaging for candles, made possible by the disclosed composition being semi-liquid in nature.

This novel composition is capable of carrying a much higher concentration of fragrance oil than what could be added to a traditional solid candle, while retaining a stable uniform consistency. The high fragrance oil concentration results in a more liquid candle with substantially stronger and longer lasting scent. In a traditional solid candle, the addition of this much oil would cause consistency and uniformity problems. These problems are eliminated by the disclosed composition.

Due to the high concentration of fragrance oil, the scent from the disclosed semi-liquid candle begins to throw even without the addition of any heat at all, making this an excellent product for applications where burning a candle is not permitted or where the unavailability of electricity makes the use of a warmer impossible. Since simply opening the package releases a high level of fragrance, this product may be packaged and marketed as a car fragrance product.

Upon addition of low levels of heat, the fragrance becomes quite intense. It is so intense that it could be used in outdoor environments where the natural ventilation would typically eliminate the desired fragrance produced by traditional candles. As a result, the disclosed could easily produce desired fragrance for outdoor venues, even containing Citronella oil for mosquito control.

The melting point of the composition is far lower than that of solid paraffin or even soy based candles, beginning around 90 degrees. Traditional warmers heat up to 160 degrees. When the disclosed composition is used with a traditional warmer, the fragrance throw is far more intense and longer lasting than any type of candle currently known in the art. The surprisingly intense fragrance achieved enables the user to scent their homes using only a very small amount of the semi-liquid candle substance. The composition has a more appealing scent, however, than warming solely fragrance oil, as the disclosed invention throws off a scent more similar to that emitted from burning a wicked candle.

Because only a small amount of the disclosed composition is needed to achieve the desired fragrance, and because it is in a semi-liquid state, the composition can be packaged and sold in very small containers, saving money in terms of shelf space, shipping and materials. This enables the composition to be packaged in small aesthetic packages such as flip top or screw top plastic tubes or small squeeze packets similar to the size and shape of a ketchup packet, which enables retailers to sell the product on "impulse buy" racks near checkout.

When used herein, the term "petroleum jelly" may be used interchangeably with "soft petroleum wax", "petrolatum" and the terms are indicated to refer to a semi-solid mixture of hydrocarbons which will typically have a carbon content higher than 20 carbon atoms per molecule.

When used herein, the term "candle" refers to a heat engaged, scent emitting fragrance product and is not intended to limit the disclosure to traditionally recognized wicked or wickless candles. The term "candle" has traditionally referred to a solid object and is only used herein to provide a reference point of the disclosed method and composition, which is a semi-liquid, rather than solid object.

The petroleum jelly used herein is far different than paraffin wax which is traditionally used in candle making and, unlike petroleum jelly, maintains a solid state at room temperature and has a much higher melting point of 117 to 147 degrees Fahrenheit.

The disclosed invention is distinguished from the currently known candle compositions and methods by several important factors including improved affordability, environmental soundness, and a higher quality product.

First, the wickless semi-liquid squeeze candle invention disclosed herein contains no wick, instantly making it safer and cleaner in terms of eliminating fire risk, smoke and soot.

Second, the semi-liquid composition features a significant breakthrough in candle composition, solving several disadvantages inherent in the prior art. The disclosed semi-liquid composition enables capture of a very high concentration of fragrance oils, for example, 20% and even up to 50%, while retaining a more candle like scent and a more package-able and uniform consistency. A candle composition of a semi-liquid state, that allows capture of very high levels of fragrance oils, has been heretofore unknown.

The packaging possibilities of a semi-liquid composition are varied and advantageous. The disclosed composition can be packaged in small, for instance one ounce, squeezable packets or flexible plastic tubes having an opening at one end. This type of packaging is significantly less expensive both to manufacture and to ship, due to its extremely light weight. When compared to the glass jars that either solid or liquid candles are packaged and shipped in, the cost savings merits attention. The breakage factor of glass jars are also eliminated.

The use of small squeezable packets is appealing on many levels. Consumers quickly tire of the same scent and often grow weary of a large candle jar, long before it has been fully used. With the achievement of a stable and uniform semi-liquid composition, a customer can buy several different scented packets for less than they would spend on one candle in a jar or one package of candle wax blocks. A semi-liquid composition, packaged in a squeezable tube, enables controlled dispensing of product. The controlled dispensing aspect enables the end user to “mix and match” various proportions of varying fragrances, achieving truly customizable scents. Although the popular candle wax blocks somewhat cater to this goal as well, the blocks, by their characteristics, limit the end user to a minimum amount of product, whereas the disclosed enables the end user to apply as much or as little product to the warmer as desired, controlling the level of scent in the room. This is an important advancement as some individuals, due to heightened sensitivity or allergies, may desire only a very subtle scent. The fragrance intensity control does not exist in currently known products. As the disclosed has a much more intense fragrance (and faster acting) than the blocks, the end user will save money by using less product to achieve the desired fragrance intensity.

The package may have a zip seal or, in the case of a tube, a cap, allowing re-closure to maintain strength of scent and prevent mess Because there is very little cost in the packaging and shipping of the disclosed, the consumer cost can be expected to be nearly half of what a traditional candle would cost on a per ounce basis and the fragrance time per ounce could easily be as much as five times longer per ounce compared to products on the market today. From a marketing standpoint, the product will take very little shelf space, and the small packets could even be hung on floor standing or counter standing spindles or racks, taking up no shelf space and creating a bright colored, high fragrance, small, inexpensive impulse buy item that will easily fragrance a whole home, more intensely and for longer than candles currently available.

The disclosed composition exhibits a stable, attractive, uniformly-colored (when colorant is optionally used) product. To use the disclosed invention, one merely opens the small squeezable packet or tube, squeezes a few grams worth on a small dish positioned in conjunction with an electrically powered warmer and turns the warmer on. The fragrance begins releasing into the environment quickly, even before heat is applied. As the temperature approaches 90° F., the semi-liquid consistency begins to turn to liquid. Having less than one teaspoon of 90° F. liquid, versus a whole candle jar of several ounces of 160° F. is a far safer condition for children and pets who may touch the liquid. It is also far less prone to spills than liquid candles or straight liquid fragrance oils.

At the same time, the scent released by the disclosed invention is more similar to that of a traditional wicked burning candle. Most consumers find the traditional scent more appealing than just the smell of a warmed fragrance oils, as the smell of the wax melting and blending with the candle fragrance adds a whole other dimension to the fragrance.

The disclosed composition works well with color dyes, the proportions of resin and jelly mixing to achieve a smooth, uniform attractive consistency.

In the preferred embodiment, a hydrogenated plasticizer known as hydrogenated methyl ester of rosin was used as the resin choice to mix with a base of petroleum jelly and fragrance oil. In the percentages and their equivalents described use of the hydrogenated methyl ester of rosin in the described composition caused a high quality formulation that exhibited all the disclosed advantages. Other resins or plasticizers could be used if they provided similar results and had similar characteristics such as low odor, resistance to aging, similar consistency and other considerations as described herein. A very soft candle wax, soft petroleum wax or petroleum jelly may be used as the base. This creates a semi-liquid consistency, yet, one that in conjunction with the appropriate proportions of the described resin, was surprisingly found to enable uniform consistency, stability, low melting threshold, and capture of unusually high concentrations of fragrance oils. The disclosed composition does not dry out, the way a water based liquid or semi-liquid candle would.

Turning to the illustrations, as exhibited in FIG. 1, in a preferred embodiment, the disclosed invention may be packaged in a small plastic squeezable packet 10 containing as little as less than one ounce. In FIG. 1 the packet 10 is shown as rectangular although a variety of whimsical and traditional shapes could be utilized, including round, heart shaped, and any other shape desired to improve aesthetic quality and marketability. The packaging may be clear, to show off the colorful squeeze candle inside, or may be any other wrapper type as desired. Tubes or other types of packaging may be employed for packaging as desired. The packet may have a tear off strip or corner, or as illustrated in FIG. 1, have a re-sealable plastic zipper lock 12. It is apparent that the semi liquid composition could be packaged in any number of other possible containers, including squeeze bottles, tubes similar to toothpaste tubes, and other containers, having flip top or twist off lids.

The concept of containing a candle composition in a small plastic packet or tube however is, as explained above, clearly advantageous in the marketplace, new in the art and is only possible using the semi-liquid composition disclosed herein.

Figure 2:
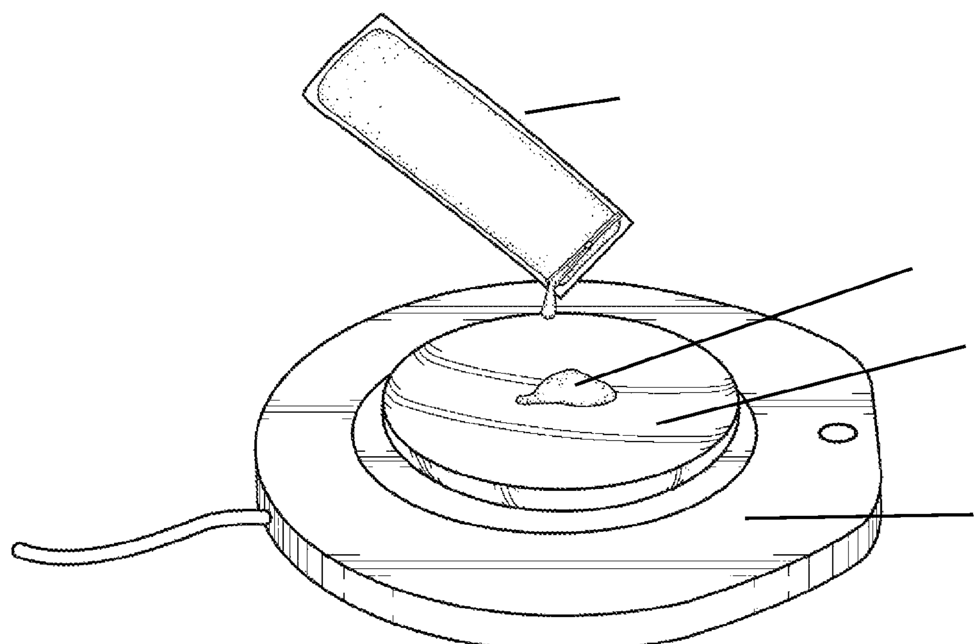
FIG. 2 is a side perspective view of a preferred embodiment of the invention, being applied to a warmer.

As illustrated in FIG. 2, the disclosed squeeze candle composition 14 is used by squeezing a small amount into a dish 16 that is situated on a warmer 18, which warmer 18 is then plugged into an electrical outlet to warm the dish 16 and its contents. As the composition 14 is heated, more intense fragrance is released into the environment.

Figure 3:
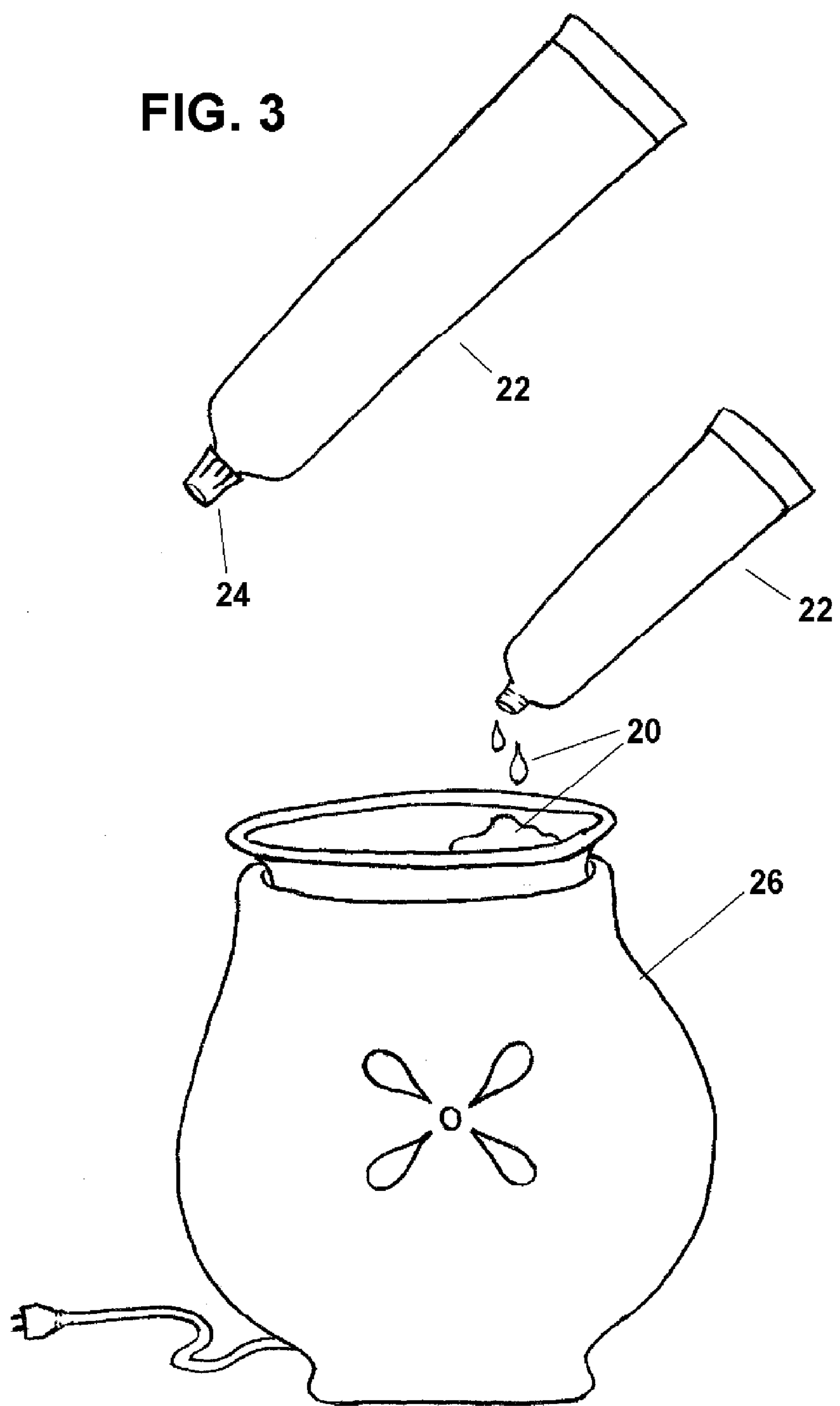
FIG. 3 is a side perspective view of a preferred embodiment of the invention.

FIG. 3 illustrates the preferred embodiment of the semi-liquid composition 20 being squeezed from the tube 22 after the cap 24 is removed, the composition 24 accumulating on the warmer 26. Most warmers are then plugged into the wall to provide the heating element, although battery and other forms of power are acceptable. FIG. 3 illustrates the tube embodiment as opposed to the packet embodiment of FIGS. 1 and 2. The tube is preferable as it is more easily resealable although the packets are a viable alternative embodiment.

Experiment

Traditional wicked solid candles, typically throw fragrance for 8-10 hours per ounce, provided the wick is kept properly trimmed.

An experiment was performed with the disclosed invention, to determine the advantages of the disclosed composition. 4 grams of the disclosed composition was squeezed (approximately 15% of one ounce) of the disclosed composition onto a warmer plate. The preferred embodiment composition contained 40% watermelon fragrance oil, 15% hydrogenated methyl ester of rosin, a fraction of a percent of color dye, and the remainder (over 45%) petroleum jelly. The warmer reached a high temperature of 160° F. The fragrance easily threw a 2,000 square foot home for 26 hours, far outperforming currently known candles. It did not dry out.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It is to be understood that the embodiments disclosed herein are shown for illustrative purposes and are not intended to be construed as limitations of the disclosed method and system. Those skilled in the art will recognize or be able to ascertain in the course of routine experimentation, that variations and equivalents of the embodiments may be undertaken without departing from the scope of the invention.

Certain terms are used throughout the description to refer to particular method components. As one skilled in the art will appreciate, design and manufacturing companies may refer to a component by different names. This document does not intend to distinguish between components that differ in name but not function.

The terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other intermediate devices and connections. Moreover, the term "method" means "one or more components" combined together. Thus, a method can comprise an "entire method" or "sub methods" within the method.

The use of the word "a" or "an" when used in conjunction with the word "comprising" may mean "one", or may also mean "one or more." The use of the term "or" in the claims is used to mean "and/or" unless explicitly indicated to refer to alternatives only or the alternatives are mutually exclusive, although the disclosures supports a definition that refers to only alternatives and "and/or."

The methods and systems disclosed and claimed herein can be made and executed without undue experimentation based on the level of disclosure presented. While the methods and systems have been described in terms of their preferred embodiments, it will be apparent to those skilled in the art that they are not limited to the exact steps described and may vary from such description without departing from the scope and spirit of the invention. The substitutes and modifications employed by one skilled in the art are deemed to fall within the scope of the invention.

What is claimed is:

1. A semi-liquid candle composition, the composition consisting essentially of at least 40% petroleum jelly by weight, at least 10% hydrogenated plasticizer by weight and at least 20% fragrance oil by weight, wherein the composition has the characteristic of a melting point between 90 degrees and 180 degrees Fahrenheit and further has the characteristic of a stable semi-liquid consistency at room temperature.

2. The composition of claim 1 wherein the hydrogenated plasticizer percentage by weight is 10% to 15%.

3. The composition of claim 1 wherein the petroleum jelly percentage by weight is 40% to 65%.

4. The composition of claim 1 wherein the fragrance oil percentage by weight is 20% to 50%.

5. The composition of claim 1 wherein the petroleum jelly percentage by weight is 60-65%.

6. The composition of claim 1 wherein the fragrance oil percentage by weight is 20-25%.

7. The composition of claim 1 wherein the hydrogenated plasticizer percentage by weight is 15%.

8. A candle composition, the composition consisting essentially of at least 40% petroleum jelly by weight, at least 10% hydrogenated methyl ester of rosin by weight and at least 20% fragrance oil by weight, wherein the composition has the characteristic of a melting point between 90 degrees and 180 degrees Fahrenheit and further has the characteristic of a stable semi-liquid consistency at room temperature.

9. The composition of claim 8 wherein the composition has the characteristic of a melting point between 90 and 110 degrees Fahrenheit.

10. The composition of claim 8 wherein the composition has the characteristic of a melting point between 110 and 120 degrees Fahrenheit.

11. The composition of claim 8 wherein the composition is contained in a squeeze container having a closeable opening at one end.

12. The composition of claim 8 wherein the hydrogenated methyl ester of rosin percentage by weight is 10% to 15%.

13. The composition of claim 8 wherein the petroleum jelly percentage by weight is 40% to 65%.

14. The composition of claim 8 wherein the fragrance oil percentage by weight is 20% to 50%.

15. A scent releasing device, the device comprising:

a composition comprising petroleum jelly, hydrogenated methyl ester of rosin, and fragrance oil, the composition having the characteristic of maintaining a semi-liquid consistency at room temperature and further having the characteristic of a melting point between 90 and 180 degrees Fahrenheit;

a squeezable container for containing the composition until use, the container having a closeable opening at one end for dispensing of the composition in controllable amounts.

* * * * *